United States Patent [19]

Acholla

[11] Patent Number: 5,394,733
[45] Date of Patent: Mar. 7, 1995

[54] QUANTITATIVE PYROLYSIS-GAS CHROMATOGRAPHY USING DIAMONDOID COMPOUNDS

[75] Inventor: Francis V. Acholla, Yardley, Pa.

[73] Assignee: Mobil Oil Corporation, Fairfax, Va.

[21] Appl. No.: 265,352

[22] Filed: Jun. 24, 1994

[51] Int. Cl.$^6$ .................. G01N 1/22; G01N 33/18
[52] U.S. Cl. .................. 73/23.41; 73/23.38; 73/19.02; 73/23.35
[58] Field of Search .............. 73/19.01, 23.38, 23.41, 73/19.02, 23.35

[56] References Cited

U.S. PATENT DOCUMENTS

| 3,425,807 | 2/1969 | Levy | 73/23.41 |
| 3,438,242 | 4/1969 | Ayers et al. | 73/23.41 |
| 3,478,205 | 11/1969 | Sporek | 73/23.41 |
| 3,715,910 | 2/1973 | Fore et al. | 73/23.1 |
| 4,159,894 | 7/1979 | Hu | 23/230 PC |
| 4,357,836 | 11/1982 | Kokesh | 73/863.11 |
| 4,536,199 | 8/1985 | Toon | 55/67 |
| 4,629,702 | 12/1986 | Fan | 436/32 |
| 5,201,219 | 4/1993 | Bandurski et al. | 73/153 |
| 5,240,604 | 8/1993 | Cortes et al. | 210/198.20 |
| 5,312,756 | 5/1994 | Jolly | 436/8 |

OTHER PUBLICATIONS

Improved kerogen typing for petroleum source rock analysis, Larter et al., Nature, vol. 318 (1985).
The control of maturity and kerogen type on quantitative analytical pyrolysis data, Oygard et al., Organic Geochemistry, vol. 13, 1153 (1987).
The micro-scale simulation of maturation: outline of a new technique and its potential application, Horsfield et al., Geologische Rundschau, 78 361 (1989).
Kerogen maturation in a reference kerogen Type II series: the Toarcian shales of the Hils syncline, NW Germany, Vandenbroucke et al., Org. Geochem., vol. 20 No. 7, pp. 961–972 (1993).
Occurrence and significance of prist-1-ene in kerogen pyrolysates, Larter et al., Nature, vol. 279, 405, (1979).
Characterization of petroleum source rocks and shales by pyrolysis-gas chromatography-mass spectrometry-multiple ion detection, Philp et al., Org. Geochem., vol. 6, pp. 489–501 (1984).
Characterization of asphaltenes by pyrolysis-field ionization mass spectrometry-some observations, Wilhelms et al., Org. Geochem., vol. 20 No. 7, pp. 1049–1062 (1993).

Primary Examiner—Hezron E. Williams
Assistant Examiner—J. David Wiggins
Attorney, Agent, or Firm—Alexander J. McKillop; Dennis P. Santini; Lori F. Cuomo

[57] ABSTRACT

A method for the quantitative determination of oil and gas formation in pyrolysis-gas chromatography. A diamondoid compound, such as adamantane, is used as an internal standard in pyrolysis-gas chromatography to quantitate oil and gas yields from kerogens on pyrolysis. Diamondoid compounds are thermally stable and chemically unreactive with pyrolysis reaction products during oil and gas formation.

8 Claims, 2 Drawing Sheets

QUANTITATIVE PYROLYSIS-GAS CHROMATOGRAPHY USING DIAMONDOID COMPOUNDS

FIELD OF THE INVENTION

The invention relates to a method for the quantitative determination of oil and gas formation in pyrolysis of kerogens, source rocks and macerals.

BACKGROUND OF THE INVENTION

In the field of geochemical research and petroleum exploration, an area of growing interest is analysis of geological samples to determine the remaining petroleum generating potential of the rock sample. Work in this field has been directed to methods for removing hydrocarbons from geological samples and analyzing the hydrocarbons, to apparatuses for laboratory and field analysis for geological samples, and to the development of theoretical and practical models for predicting petroleum exploration related characteristics for the raw data obtained.

Direct assessment of actual petroleum potential for any kerogen (insoluble organic portion of a sedimentary rock) system is vital for Sedimentary Basin Modelling in oil exploration. Pyrolysis-gas chromatography (pyrolysis-GC) techniques have proven successful in providing vital information in determining kerogen characteristics, oil-source rocks correlations, petroleum generation kinetics, gas-oil ratios (GOR) and precursor product relationships with a view, among others applications, to determining catagenic petroleum yield and composition. However, conventional pyrolysis-GC fingerprinting is often a subjective process and therefore to be useful, kerogens should be classified at the same molecular level, as is possible with crude oils; thus full quantitation of all pyrolysis products is desirable.

In performing analyses of the type described above, it is desirable to be able to make accurate, reproducible determinations of quantity of volatile hydrocarbons present in the geological sample.

Hydrocarbons may be quantitated using a methylstyrene internal standard generated during the pyrolysis process from polymethylstyrene admixed with kerogen as discussed in Larter et al. Nature (London) 318, 277,278 (1985) Poly-para-t-butyl-styrene has been similarly used. See Oygrad et al., Org. Geochem., 13, 1153 (1988). In addition, products are also quantified with reference to phenylhexane, both external and internal, by peak area integration. See Horsefield et al., Geol. Rund., 78, 361 (1989).

Quantification is also done by gas chromatography using the branched and cyclic hydrocarbon fraction of a crude oil as an external standard. See Vandenbroucke et al., Org. Geochem., 7,961 (1993). However, the above internal and external standards are generally thermally unstable and chemically reactive with the potential of forming reaction products which could interfere with peaks of interest during sealed tube pyrolysis.

Therefore it is an object of the present invention to provide an on-line quantitative pyrolysis-GC method whereby the internal standard is thermally stable during oil and gas generation temperatures. It is a further object of the present invention to provide an on-line quantitative pyrolysis-GC method whereby the internal standard is chemically unreactive during oil and gas generation temperatures.

SUMMARY OF THE INVENTION

In efforts to develop a quantitative pyrolysis-GC method, it has now been found to use a diamondoid compound as an internal standard in pyrolysis-GC to quantitate gas and oil yields from carbon and hydrogen containing materials capable of generating oil and gas, such as kerogens, on pyrolysis. The method of the present invention is superior to conventional methods because of the inherent thermal stability of diamondoid compounds, such as adamantane, which is due to its fused ring diamond like structure. The use of adamantane as an internal standard provides a simple direct means of quantitation of oil and gas generated from source macerals, kerogens and coals.

The invention therefore includes a method for the quantitative determination of oil and gas formation in pyrolysis-gas chromatography comprising:
  pyrolyzing a weighed sample of carbon and hydrogen containing material capable of generating oil and gas admixed with diamondoid compound under an oxygen deficient atmosphere at a temperature of at least about 250° C. to produce pyrolysis gas;
  analyzing the pyrolysis gas by gas chromatography; and
  quantitating with reference to diamondoid compound standard peak area integration.

DETAILED DESCRIPTION OF THE INVENTION

Figure 1:
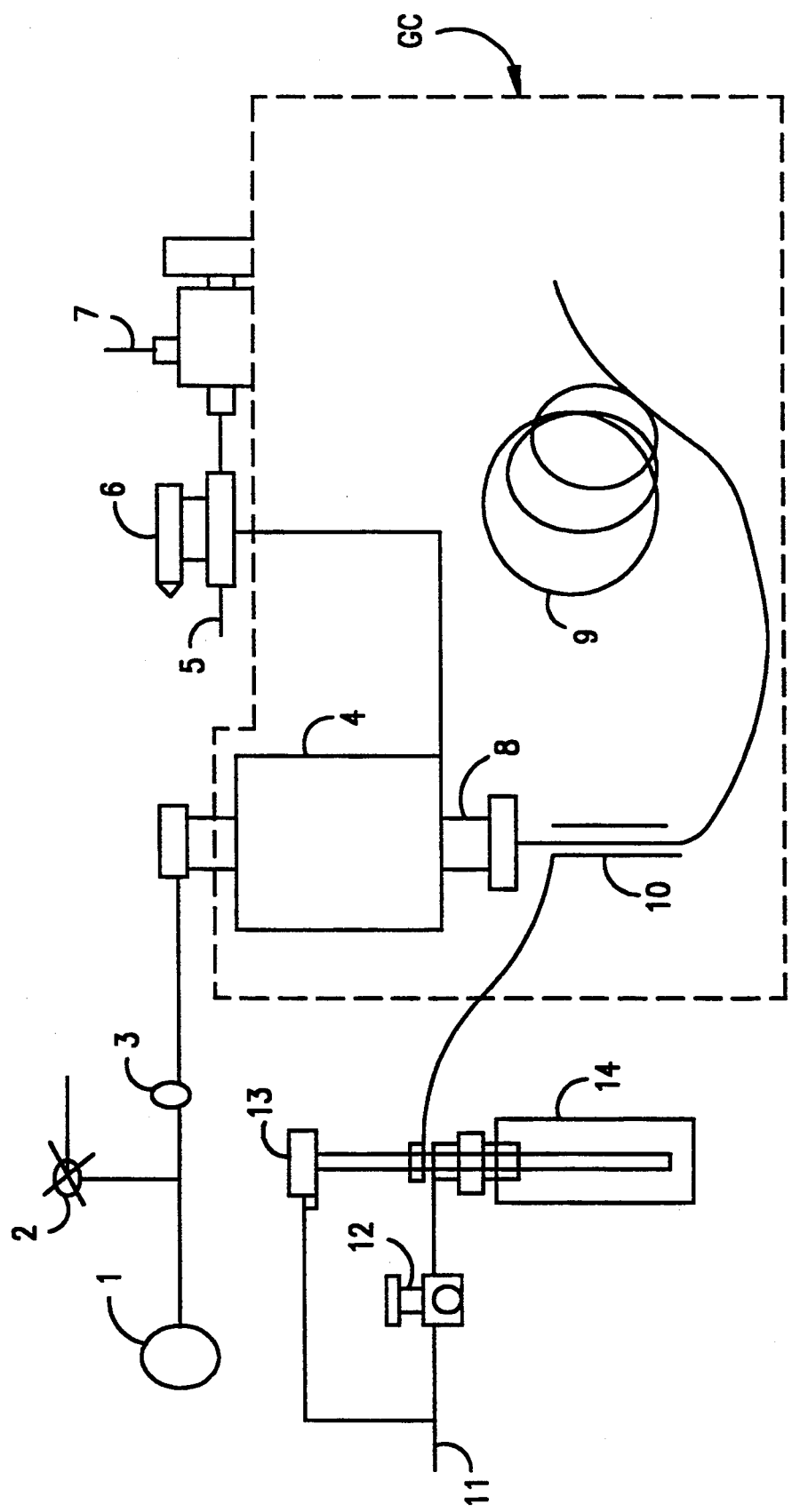
FIG. 1 is a simplified schematic diagram illustrating the micro-scale sealed vessel thermal analysis system used in the method of the present invention.

The present invention is related to a direct method for the quantitative determination of oil and gas formation is sealed tube pyrolysis of carbon and hydrogen containing material capable of generating oil and gas, by pyrolyzing a sample containing, for example, kerogenous material, and analyzing the pyrolysis gases by gas chromatography. A diamondoid compound is used as an internal standard. To accomplish this, a weighed sample of kerogenous material and diamondoid compound is placed under an oxygen deficient atmosphere at a temperature in the range of about 250° to about 450° C. for pyrolysis. After eluting the hydrocarbonaceous gas resulting from the pyrolyzed kerogenous material, a chromatogram is developed which shows the relationship between various hydrocarbonaceous components emitted from the kerogenous material. The products are quantified with reference to diamondoid compound internal standard peak area integration. The terms "quantitate" and "quantify" are used interchangeably throughout.

The carbon and hydrogen material capable of generating oil and gas include kerogens, asphaltenes, source rocks and macerals. Macerals are microscopically recognizable particulate organic compounds of kerogen showing distinctive physiochemical properties which change with thermal maturity. Macerals include liptinite, vitrinite and inertinite.

The term "diamondoid compounds", is used in its usual sense, to designate a family a polycyclic alkanes including adamantane, diadamantane and triadamantane, as well as the higher analogs and their substituted derivatives, examples of which include ethyl- and methyl-substituted diamondoids. For a survey of diamondoid molecules, see Fort, Raymond C., Adamantane, The Chemistry of Diamond Molecules (1976). Adamantane is preferred in the method of the present invention.

A pyrolysis unit, or modified gas chromatograph, is used for the quantitative determination method of the present invention. A rock sample is placed in a sample inlet which has been heated to the temperature of the hydrocarbon volatilization. The sample is subsequently heated to a higher temperature, generally by means of a radiant heater, to pyrolyze the remaining organic matter. A gas detection device such as a flame ionization detector responds to the quantity of hydrocarbons generated and a recorder instrument records graphically the detector response versus time. The detector responses obtained are compared with the standards developed to determine the actual quantities of hydrocarbons generated, and thus assess the petroleum potential of the sample.

Generally, the pyrolysis-GC technique for use in the method of the present invention includes adding precleaned glass beads to the elbow of flexured 40 microliter glass capillary tubes. Three microliters of 0.1M adamantane (99.9 wt. %) solution in dichloromethane is carefully added and the solvent removed under vacuum. Mild solvent may be removed under ambient conditions as well. Between 2 and 4 mg. of kerogen concentrate is weighed accurately and placed into the elbow portion of the glass capillary tubes and then additional glass beads are added to reduce the volume of the tubes to about 10 microliters. The tubes are then sealed under an oxygen deficient gas, i.e. comprising less than about 100 ppm oxygen, or an inert gas, such as argon, to minimize any oxidation and artificially matured at predetermined times and temperatures in the range of from about 250° to about 450° C., in a programmable oven.

The tubes are cracked open in the micro-scale sealed vessel-pyrolysis-GC system as shown in FIG. 1. Inert carrier gas, such as helium, is passed through line 1 to micro-scaled sealed vessel (MSSV) 4 where the tubes are cracked open with a tube breaker. The carrier gas is generally under a pressure in the range of from about 5 to about 50 psi. A sample valve 2 is provided for the introduction of a sample gas, such as methane, to measure flow rate of the system. Carrier gas flow is stopped with on/off valve 3 during sample gas introduction. Purge vent 5, three way valve 6 and split vent 7 are used in conjunction to control the flow of product gas from the vessel. The MSSV is generally operated at a temperature in the range of from about 300° to about 350° C. The products are swept from the injector port (set at 325° C.) through line 8 by the flowing helium through cold trap 10 to capillary column 9. The product gas is cryogenically focused using Teflon tubing filled with liquid nitrogen. Nitrogen gas is passed through line 11 and liquid nitrogen valve 12, pressure regulator 13 and liquid nitrogen tank 14 are used to cryogenically cool. The product gas is analyzed in the capillary column by gas chromatography after ballistic heating. Gas chromatography is discussed by McNair et al., Basic Gas Chromatography, 5th Edition, Varian Instrument Division (1969), incorporated herein by reference. The product gas is separated (by boiling point and molecular weight) and detected by, for example a flame ionization detector or mass spectrometer. After gas chromatography analysis, the MSSV can be operated at a higher temperature, generally in the range of from about 300° to about 540° C. to pyrolyze unreacted residue in the tubes. Hydrocarbons including n-alkanes ($C_1$–$C_{35}$), isoprenoid alkanes, alkyl-substituted aromatics, and nitrogen, oxygen and sulfur-containing compounds are identified using standard compounds and all products are quantified with reference to the adamantane standard peak area integration.

For example, after breaking the tube in the MSSV system and obtaining a good chromatogram, the peak area count for the adamantane from the chromatogram is used to calculate the weight of total detectable hydrocarbons by, for example, a flame ionization detector using the following formula:

$$\text{Amount of product compound} = \frac{\text{(Area of product compound peak) (Weight of diamondoid standard)}}{\text{(Area of diamondoid standard peak) (Response factor)}}$$

The amount of product compound/weight of kerogen material can be calculated by dividing the amount of product compound by the weight of kerogen. If the total organic carbon content (TOC, wt. %) is known, the data can be reported as the Amount of product compound/grams TOC. The Response factor is determined independently. However, since response factors change with instrument conditions, a response factor value of 1 for all hydrocarbons relative to adamantane is assumed.

The following examples illustrate the process of the present invention.

EXAMPLE 1

Thermal stability data for pure adamantane under closed system pyrolysis is shown in Table 1. The data indicates that adamantane is thermally stable up to about 450° C. and decomposes at 500° C. The average % recovery is based on 4 replicate runs.

TABLE 1

| Temperature (°C.) | Average % Recovery ($\pm 0.1$) n = 4 |
|---|---|
| 300.0 | 99.7 |
| 350.0 | 99.5 |
| 400.0 | 99.6 |
| 450.0 | 99.7 |
| 500.0 | 3.5 |

EXAMPLE 2

Figure 2:
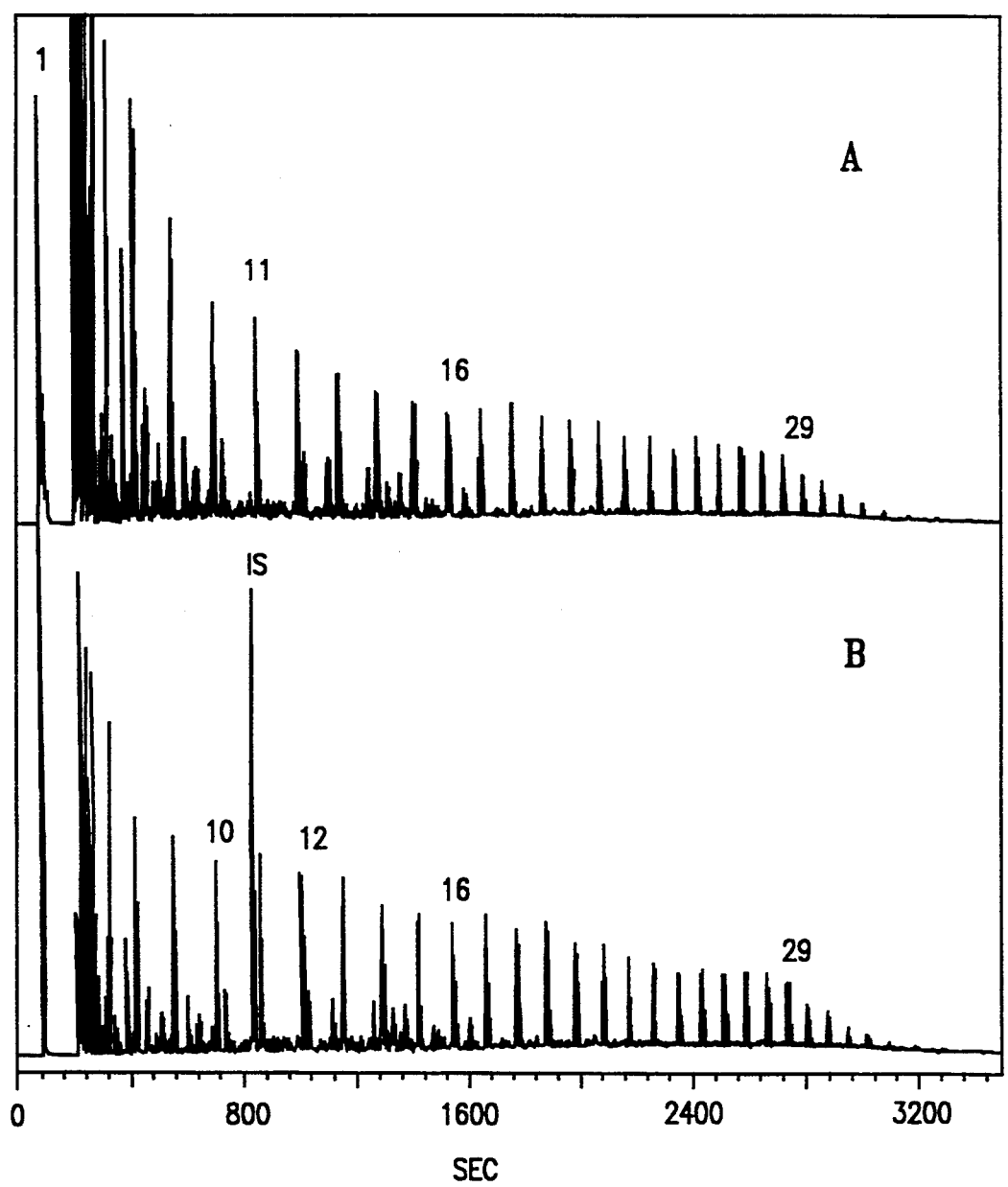
FIG. 2 is a gas chromatograph of a pyrolysis of a Green River Shale kerogen with and without adamantane.

A sample of Green River Shale kerogen is pyrolyzed using the method of the present invention with and without an internal adamantane standard. Green River Shale is a sedimentary rock, commonly laminated, that is dominated by clay size particles and shows fissility approximately parallel to bedding, having greater than about 25 wt. % carbonate. FIG. 2 shows a gas chromatogram of micro-scale sealed vessel (MSSV) pyrolyzates at 350° C./72 hours. From FIG 2, it can be seen that adamantane elutes between n-$C_{10}$ and n-$C_{11}$ hydrocarbons and does not co-elute with any major pyrolysis products.

A summary of the distribution of classes of compounds including selected oil maturity parameters are shown in Table 2. Pyrolyzate yield (mg/g total organic carbon (TOC) of the Green Shale kerogen is presented as a function of reaction temperature/72 hours. The average standard deviation is in the range of from about 5 to about 15%.

TABLE 2

| Temp. (°C.) | Total Hydrocarbons | $C_1$ | $C_2$-$C_4$ | $C_5$-$C_{15}$ | $C_{16}$-$C_{31}$ | Aromatics | Pristane | Phytane |
| --- | --- | --- | --- | --- | --- | --- | --- | --- |
| 300.0 | 50.90 | 5.55 | 8.83 | 8.22 | 10.93 | 2.45 | 1.96 | 0.63 |
| 315.0 | 87.40 | 6.76 | 15.04 | 19.83 | 16.94 | 4.31 | 1.81 | 0.59 |
| 330.0 | 140.53 | 9.66 | 24.89 | 38.82 | 25.05 | 5.77 | 1.73 | 0.52 |
| 350.0 | 229.93 | 17.05 | 46.57 | 74.54 | 28.36 | 9.85 | 0.88 | 0.32 |
| 375.0 | 575.61 | 54.95 | 189.01 | 150.20 | 6.05 | 21.89 | trace | trace |
| 400.0 | 619.32 | 96.48 | 350.33 | 47.18 | 1.87 | 47.11 | trace | trace |

Changes and modifications in the specifically described embodiments can be carried out without departing from the scope of the invention which is intended to be limited only by the scope of the appended claims.

I claim:

1. A method for the quantitative determination of oil and gas formation in pyrolysis-gas chromatography comprising:

pyrolyzing a weighed sample of carbon and hydrogen containing material capable of generating oil and gas admixed with diamondoid compound under an oxygen deficient atmosphere at a temperature of at least about 250° C. to produce pyrolysis gas;

analyzing the pyrolysis gas by gas chromatography; and quantitating with reference to diamondoid compound standard peak area integration.

2. The method of claim 1, wherein said diamondoid compound is adamantane.

3. The method of claim 1, wherein said material capable of generating oil and gas is a kerogenous material.

4. The method of claim 1, wherein said temperature is up to about 450° C.

5. The method of claim 1, wherein the diamondoid compound and carbon and hydrogen containing material capable of generating oil and gas are added in a ratio of diamondoid compound/carbon and hydrogen material of greater than about 1/200.

6. The method of claim 1, wherein a flame ionozation detector is used in said gas chromatography.

7. The method of claim 1, wherein a mass spectrometer is used in said gas chromatography.

8. A method for the quantitative determination of oil and gas formation in pyrolysis-gas chromatography comprising:

pyrolyzing a weighed sample of kerogenous material admixed with adamantane under an oxygen deficient atmosphere at a temperature of at least about 250° C. to produce pyrolysis gas;

analyzing the pyrolysis gas by gas chromatography; and quantitating with reference to adamantane standard peak area integration.

* * * * *